United States Patent [19]

Burkinshaw et al.

[11] Patent Number: 5,639,279
[45] Date of Patent: Jun. 17, 1997

[54] POSTERIORLY-STABILIZED PROSTHETIC KNEE

[75] Inventors: Brian D. Burkinshaw, Pfleugerville, Tex.; Lawrence D. Dorr, LaCanada, Calif.; Wayne P. Gray, Pfleugerville, Tex.

[73] Assignee: Intermedics Orthopedics, Inc., Austin, Tex.

[21] Appl. No.: 385,933

[22] Filed: Feb. 9, 1995

[51] Int. Cl.⁶ .................................................. A61F 2/38
[52] U.S. Cl. .................................................. 623/20
[58] Field of Search .............................. 623/20, 18, 21

[56] References Cited

U.S. PATENT DOCUMENTS

| | | |
|---|---|---|
| 3,638,243 | 2/1972 | Campbell, Jr. et al. . |
| 3,694,821 | 10/1972 | Moritz . |
| 3,715,763 | 2/1973 | Link . |
| 3,728,742 | 4/1973 | Averill et al. . |
| 3,748,662 | 7/1973 | Helfet . |
| 3,774,244 | 11/1973 | Walker . |
| 3,816,855 | 6/1974 | Saleh . |
| 3,824,630 | 7/1974 | Johnston . |
| 3,837,009 | 9/1974 | Walker . |
| 3,840,905 | 10/1974 | Deane . |
| 3,869,729 | 3/1975 | Attenborough . |
| 3,869,731 | 3/1975 | Waugh et al. . |
| 3,924,277 | 12/1975 | Freeman et al. . |
| 4,011,603 | 3/1977 | Steffee . |
| 4,081,866 | 4/1978 | Upshaw et al. . |
| 4,094,017 | 6/1978 | Matthews et al. . |
| 4,213,209 | 7/1980 | Insall et al. . |
| 4,224,697 | 9/1980 | Murray et al. . |
| 4,298,992 | 11/1981 | Burstein et al. . |
| 4,501,031 | 2/1985 | McDaniel et al. ............ 623/20 |
| 5,147,405 | 9/1992 | Van Zile et al. ............... 623/20 |
| 5,181,925 | 1/1993 | Houston et al. ............... 623/20 |
| 5,330,532 | 7/1994 | Ranawat ........................ 623/20 |
| 5,370,699 | 12/1994 | Hood et al. .................... 623/20 |

FOREIGN PATENT DOCUMENTS

| | | | |
|---|---|---|---|
| 0381352 | 8/1990 | European Pat. Off. ......... 623/20 |
| 2701387 | 8/1994 | France ............................ 623/20 |
| 2067412 | 7/1981 | United Kingdom . |
| 9004369 | 5/1990 | WIPO . |

OTHER PUBLICATIONS

Insall, J., Scott, N.W., and Ranawat, C.S., "The Total Condylar Knee Prosthesis: A Report of 220 Cases," From The Hospital for Special Surgery, Affiliated with the New York Hospital—Cornell University Medical College, New York, New York. 25 pgs.

*Primary Examiner*—David H. Willse
*Attorney, Agent, or Firm*—C. Steven McDaniel; Richard L. Robinson

[57] ABSTRACT

The present invention relates to prosthetic knee devices providing for an expanded range of translational movement without substantially reducing the risk of inadvertent dislocation of the knee when implanted. The devices of the invention achieve the expanded range of motion without requiring a substantial posterioral shifting of the points of contact between the femoral and tibial components. The prostheses of the invention also reduce the risk of breakdown of the plastic components of the prosthesis and the underlying resectioned proximal tibia surface by providing an expanded, winged fixation post.

19 Claims, 12 Drawing Sheets

POSTERIORLY-STABILIZED PROSTHETIC KNEE

BACKGROUND OF THE INVENTION

A. Field of the Invention

The present invention relates to prosthetic knee devices which overcome certain limitations of existing knee prostheses, generally referred to as semi-constrained knee prostheses, and more specifically as posteriorly-stabilized knee prostheses. The present knee prosthesis provides for an expanded range of degrees of translational movement without substantially reducing the risk of inadvertent dislocation of the knee when implanted. The devices of the invention achieve the increased ranges of motion without requiring a substantial posterioral shifting of the points of contact between the femoral and tibial components. The prostheses of the invention also reduce the risk of breakdown of the underlying resectioned proximal tibia surface.

B. Description of the Related Art

When natural healing of a diseased or injured knee is not sufficient to return the affected knee to its pre-injury or pre-disease condition, a preferred alternative is knee replacement surgery where certain portions of the natural knee are replaced with implanted prostheses. There are numerous types of such prostheses. One general category of knee prosthesis is the semi-constrained knee prosthesis of which an example is the posteriorly-stabilized knee. When the cruciate ligament is removed during resectioning, a posteriorly-stabilized prosthesis must be used. These knees generally possess a femoral component with a recess capable of interacting with a protuberance (peg, post) from the surface of the tibial component in order to stabilize movement of the knee components. While such semi-constrained, posteriorly-stabilized knee prostheses have gained in acceptance in the medical community, certain limitations have been found with existing knees of this type.

In certain prosthetic knees of this type, there is substantial risk of unwanted contact between the top of the peg and the roof of the recess. In most instances, were such unwanted contact to occur, the full weight of the upper leg and body would bear down on a small and relatively insubstantial surface (the superiormost surface of the tibial peg) not designed to carry such loads. In certain existing knees, this is avoided by lowering the height of the tibial peg. However, lowering the tibial peg increases the risk of an inadvertent dislocation event. In other existing prostheses, voids are left in the roof of the recess to prevent contact of the recess roof and the top of the tibial peg.

In other designs of this general category, mechanisms are provided which upon flexing of the knee joint, cause the femoral component to move substantially posteriorly in relation to the tibial component. In certain instances this posterioral shift is required by a particular device, especially where the device is to be implanted in a resectioned knee which is not resectioned with an approximately 7° posterioral slope in the proximal tibial bone surface. In any case, such camming mechanisms increase the degree of flexure possible in those knee prostheses in which they are found and such increase flexure is generally desirable. However, in those knees where camming causes the contact points between the femoral condyles as they are nested in the tibial concavities to shift posteriorly, the tibial component must be designed to fully support the load on the knee joint at progressively more posterior positions as the knee translates through its full range of flexure and extension. Otherwise, where the tibial component does not properly support the load, softer plastic components will exhibit wear causing ultimate failure of the device and breakdown of the underlying resectioned bone surface. Where significant wear of plastic components occurs, disease conditions (osteolysis) may arise as a result of interaction of plastic particles and bone tissue. It is highly preferred to have knee prostheses with at least that degree of flexure observed in the natural knee so long as such may be achieved without increased risk of dislocation and without damage to the underlying bone surfaces.

The natural knee is capable of at least several degrees of hyperextension beyond full extension without dislocating. In certain existing prosthetic knees, little if any provision is made for extension beyond normal full extension. In some instances, this lack of hyperextension ability is a result of the need in these designs to prevent dislocation of the knee joint before and at full extension. In some of these designs, the anterior surface of the tibial peg may be essentially vertical only obtusely angled in relation to the base plane of the tibial component, abruptly ending translation upon reaching full extension. It is highly preferred to allow for at least that degree of hyperextension observed in the natural knee so long as it may be achieved in the knee prosthesis without increased risk of dislocation.

The threat of destroying the resectioned bone surface underlying a tibial implant is of equal concern along the lateral portions of the implant. In particular, such threats to lateral surfaces of the underlying bone when natural knee motions other than translational motion occur, such a lateral angulation (sometimes referred to as varus or valgus motion) consisting of a lateral sliding or rocking type motion. If the tibial component of the knee prosthesis fails to provide sufficient lateral support for such motions, the plastic components may wear and the outer edges of the bone surface underlying the unsupported tibial component medial/lateral extremes may exhibit cantilevering degradation. It is highly preferred that a prosthetic knee allow for those ranges of lateral motions which are exhibited by the natural knee so long as the medial/lateral edges of the tibial component of the prosthesis adequately protect against breakdown of the plastic components or the underlying surface of the resectioned proximal tibia.

Knee prostheses are needed with expanded ranges of translational movement without increasing the risk of dislocation of the knee. Preferably, such prostheses will achieve greater ranges of both extension and flexure as those motions are exhibited by the natural knee, and will do so without requiring a substantial posterioral shifting of the points of contact between the femoral and tibial components. Where possible, such prostheses will also reduce the risk of breakdown of the plastic components or the underlying resectioned proximal tibia surface, medially, laterally, anteriorly and posteriorly.

SUMMARY OF THE INVENTION

The present invention overcomes at least certain of these limitations of existing prosthetic knees by providing a knee prosthesis with an expanded range of translational movement without substantially increasing the risk of inadvertent dislocation of the knee when implanted. Moreover, it achieves these advantages without requiring a substantial posterioral shifting of the points of contact between the femoral and tibial components. Where possible, such prostheses will also reduce the risk of breakdown of the plastic components or the underlying resectioned proximal tibia surface.

Generally, several principal characteristics of the devices of the present invention overcome the limitations recognized in prior art devices. As opposed to existing knee prostheses, the present invention provides a knee prosthesis whose femoral component (distal femur) has a pitched-roof which may interact with a relatively tall tibial peg thereby reducing risk of contact of the top of the peg and the roof of the recess during most of translation. The tibial peg is uniquely positioned with its posteriormost surface anterior of the middle of the tibial platform. This provides for a substantial increase in the degrees of flexure possible over certain existing knee prostheses. The tibial peg also has an acutely sloped anterior surface, which in combination with the anterior panel of the pitched-roof of the recess, allows an increase over the degrees of extension possible over certain existing knee prostheses. In combination, these structures provide for substantially increased degrees of translational movement without requiring any substantial amount of posterial shifting of the contact points between the femoral and tibial components. Because there is little posterioral shifting of these contact points, there is reduced risk of posterioral breakdown of the underlying bone surface. The present invention also provides a tibial component whose medial/lateral edges are less susceptible to medial/lateral cantilevering by virtue of a winged fixation post configured to provide greater medial/lateral support to the tibial component.

More specifically, the knee joint prosthesis of the invention comprises two principal components—a distal femur and a proximal tibia. Each of these components has characteristics which contribute to the ability of the knee to provide a more natural knee-like movement without increasing risk of dislocation or breakdown of the underlying bone surface.

The distal femur is used to replace the portions of the natural femur at its distal ends, including the natural distal condyles of the natural femur. The distal femur of the prosthesis has a pair of condyles which are separated and lie side by side. The condyles each have external surfaces which are curved in a convex fashion from their anterior to their posterior portions. The curved surface is one which is smooth throughout its dimension. The condyles are also convexly curved from side to side (laterally) in a similar smooth contour. These smooth convex contours are such that they substantially conform to the contour surfaces of a natural anatomical femur.

Joining the condyles is a recess which is shaped like the roof of a house pitched from a peak sloping downwardly anteriorly and posteriorly along each roof panel. The recess has a pair of spaced-apart lateral walls supporting the pitched roof. The roof itself has an anterior roof panel and a posterior roof panel. The panels meet at a peak approximately equi-distant between the extreme edges of each roof panel.

In certain embodiments, the roof panels form an included angle at the peak of approximately 146° to 154°. In yet other embodiments, the included angle is approximately 148° to 152°. In other embodiments still, the included angle is approximately 150°. In any of these embodiments, the vertex of the roof peak angle points superiorly and the resulting obtuse angle projects inferiorly. In certain embodiments, both the peak and each of the roof panels are concavely curved superiorly in order to increasingly prevent contact of the distal femur component with the proximal tibia component.

The distal femur is preferably manufactured from cast cobalt-chromium alloy, although other materials known well to those of skill in the art of implantable knee prostheses will work as well. In certain embodiments, the bone-contacting surfaces of the distal femur component may be coated with Sinterlock CSTi® (U.S. Pat. No. 5,104,410) or other surface treatment to encourage fixation of the device to the bone such as plasma spray, bone cement (polymethyl methacrylate), hydroxyapatite, grit blast, fiber mesh, beads, or the like.

The other principal component of the knee prosthesis is a proximal tibia. The platform is one having a pair of laterally separated concavities. These concavities provide for smooth motions resembling those motions of the natural knee including flexure and extension, when the condyles nest inside the concavities.

A wedge-shaped peg is located on the superior surface of the tibial platform. The peg is positioned midway between the concavities. The peg is also positioned such that its posteriormost surface is anterior to the central portion of the tibial platform. The central portion is found by determining the position of the mediolateral line bisecting the platform.

As implanted, the peg is mated with the pitched-roof recess of the distal femur in order to prevent excessive joint movements as is accomplished in the natural knee (albeit, in the natural knee, using tendons, ligaments, and cartilage discs). The structure of the pitched roof is such that contact between the roof and the top of the tibial peg is avoided throughout substantially all anteroposterior translation of the distal femur in relation to the proximal tibia. It is only beyond extension anteriorly or beyond flexure posteriorly that the roof panels contact any surface of the tibial peg, and then only the anterior or posterior surfaces, respectively.

The tibial peg has essentially parallel lateral surfaces spaced apart from the lateral walls of the pitched-roof recess. These lateral surfaces are also essentially perpendicular to a base plane of the tibial platform.

The tibial peg also has an anterior surface which is acutely angled in relation to the base plane of the tibial platform. The peg also has a posterior surface which is transversely or laterally curved outwardly or convexly. The posterior surface of the tibial peg, similarly to the lateral surfaces of the peg are essentially perpendicular to the base plane of the platform. There is no requirement for a curved surface at the base of the post to be used as a cam or to otherwise interact with the posterior roof panel of the femur.

Tibial components are preferably manufactured from ultra-high molecular weight polyethylene although similar materials known well to those of skill in the art of implantable knee prostheses may be used (L'Insalata, J. L., et al.; Scuderi, G. R., et al.; Ranawat, C. S., 1988; Goldberg, V. M., et al.; Apel, D. M., et al.; Rand, J. A.; Ranawat, C. S., et al., 1988; Wright, T. M., et al., 1989; Wright, T. M., et al., 1986; Engh, G. A., et al.; Bartel, D. L.; Chillag, K. J. et al.; and Mintz, L., et al.). In certain embodiments, metals such as CoCr may be used as a backing on bone-contacting surfaces according to techniques known well to the same skilled artisans. The anterior/posterior and medio/lateral dimensions of the tibial component is selected to provide a minimum of 85 percent total coverage of the resected tibial surface (Uematsu, O., et al.).

The relative positions and shapes of the anterior surfaces of the tibial peg and those of the femoral recess are such that, at and near full extension, the anterior surfaces are spaced apart. This is the case even where, as implanted in a resectioned knee, an approximate 7° posterioral slope has been imparted to the resectioned proximal tibia. The prostheses may also be described and viewed without imparting such a 7° bias. If this is done, then in certain embodiments, the peg and recess anterior surfaces remain spaced apart until at least approximately 7° to 12° of hyperextension. In yet other embodiments, the anterior surfaces of the peg and recess remain spaced apart until at least approximately 9° to 10° of hyperextension. In other embodiments still, the anterior surfaces of the peg and recess remain spaced apart until at least approximately 10° of hyperextension.

In order to further protect against breakdown of the plastic components of the device or of the underlying honey surfaces, there is attached to an inferior surface of the proximal tibia, a winged fixation post. The fixation post is one having at least one pair of lateral wings attached to it, and in certain embodiments at least one other pair. The wing portion of the post extends superiolaterally from an inferiormost portion of the post fixation post to a pair of attachment points on the tibial platform's inferior surface. The inventors of the present invention determined that in order to provide the necessary support for the tibial platform, that the attachment points must be separated by a length equal to or greater than approximately 25% of the proximal tibia's lateral width.

The relative positions and shapes of the posterior surfaces of the tibial peg and femoral recess are constructed such that the convexly curved posterior peg surface matingly conforms to the concavely curved posterior roof panel. First contact of the posterior roof panel of the femoral recess against the posterior surface of the tibial peg occurs somewhat above the juncture between the peg and the tibial platform, and above any incidental machined curvature at the base of the peg. From this first contact throughout the remaining flexure motion, the concavely curved posterior roof panel stays in mated and conforming contact with the convexly curved posterior surface of the tibial peg. After the initial contact between the two posterior surfaces, the posterior roof panel portion begins an almost immediate ascent superiorly along the posterior surface of the tibial peg. In so doing, the combined motion allows the prosthesis to greatly expand the range of flexure possible without causing a substantial amount of posterioral camming of the contact points between the femoral and tibial components.

The first contact between the two posterioral surfaces does not occur at or even near full flexure. At that point in the flexing motion, the posterior surfaces are spaced apart. This spacing apart is accomplished chiefly by virtue of the placement of the posterior surface of the tibial peg anterior to the line laterally bisecting the tibial platform. In certain embodiments, these posterior surfaces remain apart until at least approximately 80° to 95° of flexure. In other embodiments, these posterior surfaces remain spaced apart until at least approximately 84° to 93° of flexure. In yet other embodiments, these posterior surfaces remain spaced apart until at least approximately 84° of flexure.

As pointed out previously, the flexure made possible by the construction of the prostheses as shown by the present invention is achieved without substantially shifting posteriorly the points of contact between the condyles and the concavities by more than approximately 1 to 9 millimeters. In other embodiments, this shifting posteriorly of the points of contact is no greater than approximately 3 to 7 millimeters. In other embodiments still, the shifting posteriorly of the points of contact is no greater than approximately 5 millimeters.

Femoral rotation and/or rotationally malpositioned components, coupled with excessive horizontal laxity in the joint space have been reported to be contributing factors in dislocation of posteriorly-stabilized knee prostheses. When there is sufficient laxity, it is possible for the femur to translate anteriorly on the tibia resulting in posterior subluxation. An angle, referred to herein as the angle of antisubluxation, exists for each prosthetic knee which is predictive of the probability of posterior subluxation. The greater the angle of antisubluxation, the greater the possibility that a joint will sublux when there is excessive laxity on the joint. The femoral component of the present design addresses the tendency to sublux, in certain embodiments, by placement of an antisubluxation lip or rib along the anterior extremity of the anterior roof panel.

The following figures and descriptions will provide exemplary details as to certain preferred knee prostheses of the present invention.

BRIEF DESCRIPTION OF THE DRAWINGS

FIG. 2. (A) Right side elevation of distal femur. (B) Section CC of FIG. 1 bisecting the right femoral condyle from anterior to posterior and projecting toward the left side. (C) Section BB of FIG. 1 bisecting the distal femur from anterior to posterior and projecting toward the left side.

FIG. 3. (A) Section AA of FIG. 1 bisecting the distal femur from side to side and projecting toward the anterior. (B) Section JJ of FIG. 1 obliquely transecting the distal femur from the left anterior condyle to the right posterior condyle and projecting generally in an anterior direction.

FIG. 5. (A) Posterior elevation of proximal tibial insert, depicting in partial dashed outline the contours of each tibial concavity. (B) Posterior side elevation of an all-polyethylene proximal tibia with integral fixation post, depicting in partial dashed outline the contours of each tibial concavity bisecting the proximal tibia from side to side and projecting toward the inferior surface of the proximal tibia, with partial cutaway on right posterior portion showing underlying construction of proximal tibia.

FIG. 6. (A) Inferior surface elevation of proximal tibial insert without integral fixation post. (B) Inferior elevation of proximal tibial baseplate or all-polyethylene tibia, either with integral fixation post.

FIG. 9. (A) Section BB of FIG. 7 bisecting the proximal tibial insert, laterally and projecting toward the posterior. (B) Section BB of FIG. 7 (of an all-polyethylene tibia with integral fixation post) bisecting the proximal tibia laterally and projecting toward the posterior.

FIG. 10. (A) Section CC of FIG. 7 bisecting the proximal, in the anterior/posterior direction, through a line slightly offset to the right of the anterio/posterior midline of the proximal tibia and projecting toward the left side. (B) Section CC of FIG. 7 (of an all-polyethylene tibia with integral fixation post), bisecting the proximal tibia in the anterior/posterior direction, through a line slightly offset to the right of the anterio/posterior midline of the proximal tibia and projecting toward the left side.

FIG. 12. Assembled knee prosthesis, bisected anterio-posteriorally through both components, depicted at a fixed 7° posterior slope: (A) hyperextension; (B) full extension; (C) 30° flexion; (D) 60° flexion; (E) initial contact angle of posterior surfaces of distal femur and proximal tibia; and, (F) flexion beyond first contact.

DESCRIPTION OF PREFERRED EMBODIMENTS

Referring now to the figures, it can generally be seen that: FIGS. 1–4 depict various views of the distal femur component of the prosthetic knee device of the invention; FIGS. 5–11 depict various views of the proximal tibia component of the prosthetic knee device of the invention; FIGS. 12, 13 depict various views of the assembled knee prosthesis of the invention in various stages of extension and flexure.

Figure 1:
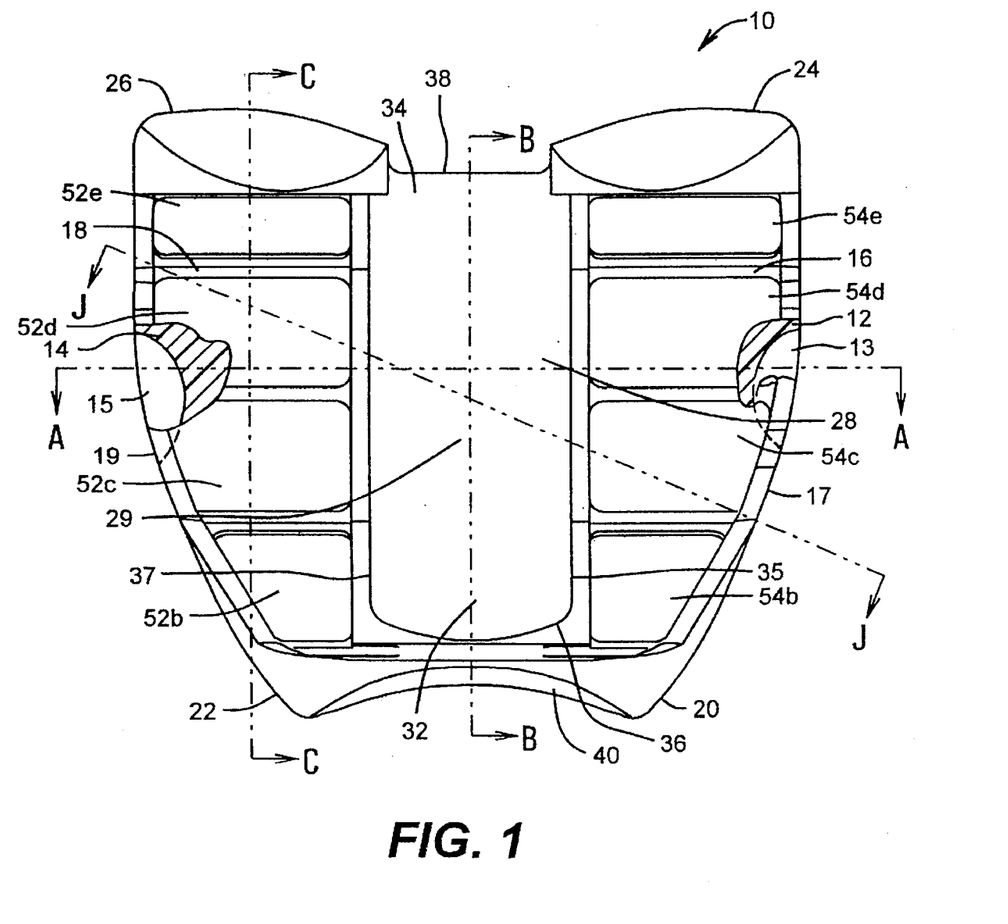
FIG. 1. Superior elevation of distal femur with partial cutaway portions on the left and right sides exposing underlying construction of walls.

FIG. 1 shows a superior elevation of the distal femur component 10 with partial cutaway portions on the left 12 and right 14 sides exposing the underlying construction of the device walls and extraction slots 13, 15, respectively, which facilitate extraction of the component removal or revision be required. Sections AA, BB, CC, and JJ will be discussed below. Distal femur 10 has a pair of condyles 16, 18 which are separated and lie side by side, to the left and right, respectively. Condyles 16, 18 each have external surfaces 17, 19, respectively, which are curved convexly from their anterior portions 20, 22, respectively, to their posterior portions 24, 26, respectively. The condyles are also laterally convexly curved in a similar smooth contour.

Joining condyles 16, 18 is a recess 28 which is shaped anteriorly and posteriorly like the roof 29 of a house pitched from a peak 30 (not shown in FIG. 1, shown best in FIG. 2C) sloping downwardly along each of two roof panels 32, 34. Recess 28 has a pair of spaced-apart lateral walls, left 35 and right 37, supporting the pitched roof. Roof 29 itself has an anterior roof panel 32 and a posterior roof panel 34. The panels meet at peak 30 approximately equi-distant between the extreme anterior 36 and posterior 38 edges of each roof panel. The anterior portions 20, 22 of condyles 16, 18, respectively, fuse along their central portions into a patella region 40 above anterior roof panel 32. It can be seen here, and better in the figures to follow that posterior edge 38 of posterior roof panel 34, and anterior edge 36 of anterior roof panel 32, each is transversely concavely curved.

Figure 3A:
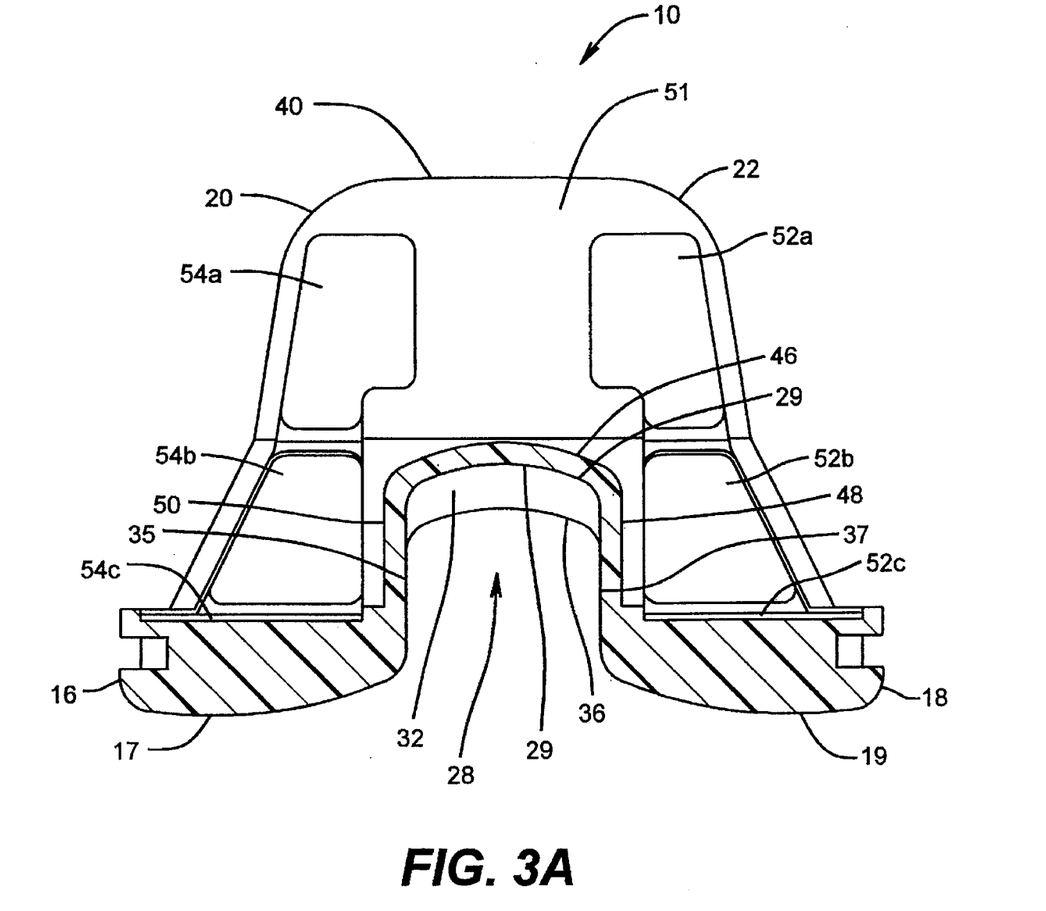
Figure 3B:
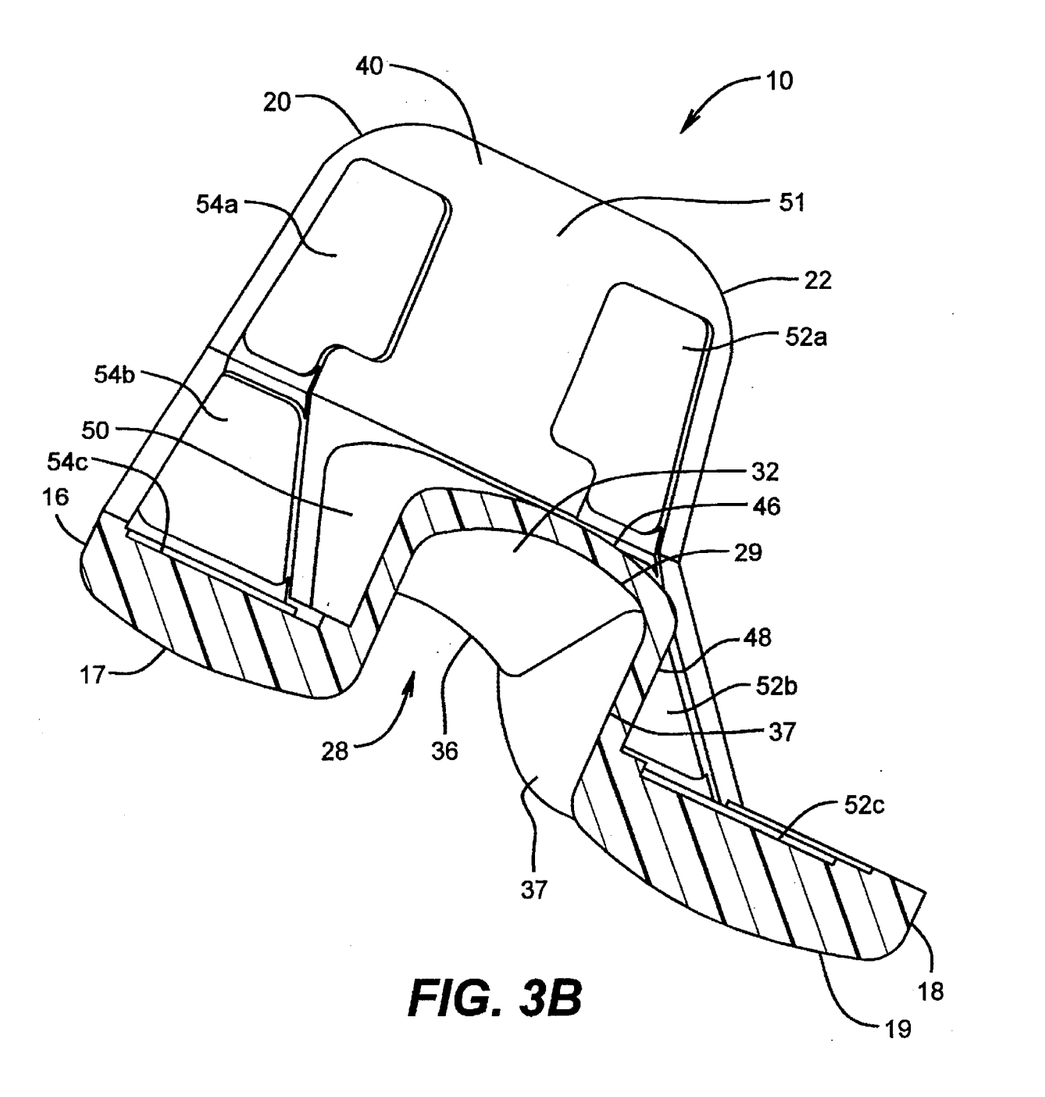
Figure 4:
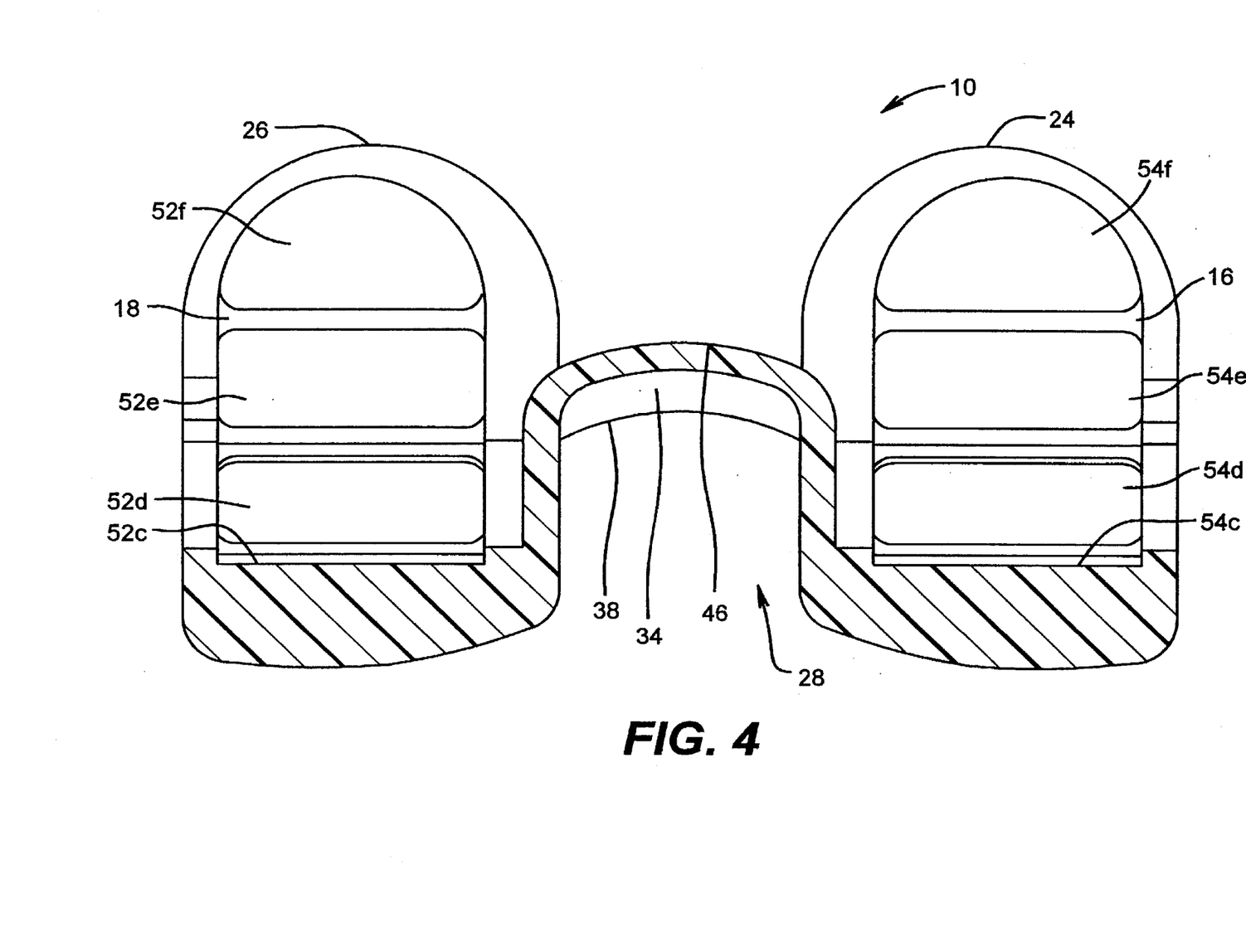
FIG. 4. Section FF of FIG. 2A transecting the distal femur laterally from inferior to superior and projecting toward the posterior.

Roof panels 32, 34 form an included angle at peak 30 of approximately 146° to 154°. The vertex of the angle at peak 30 angle points superiorly and the resulting obtuse angle projects inferiorly. As can best be seen in FIGS. 3(A–B), 4, peak 30, anterior roof panel 32, and posterior roof panel 34, are transversely, concavely curved superiorly.

Figures 2A, 2B, 2C:
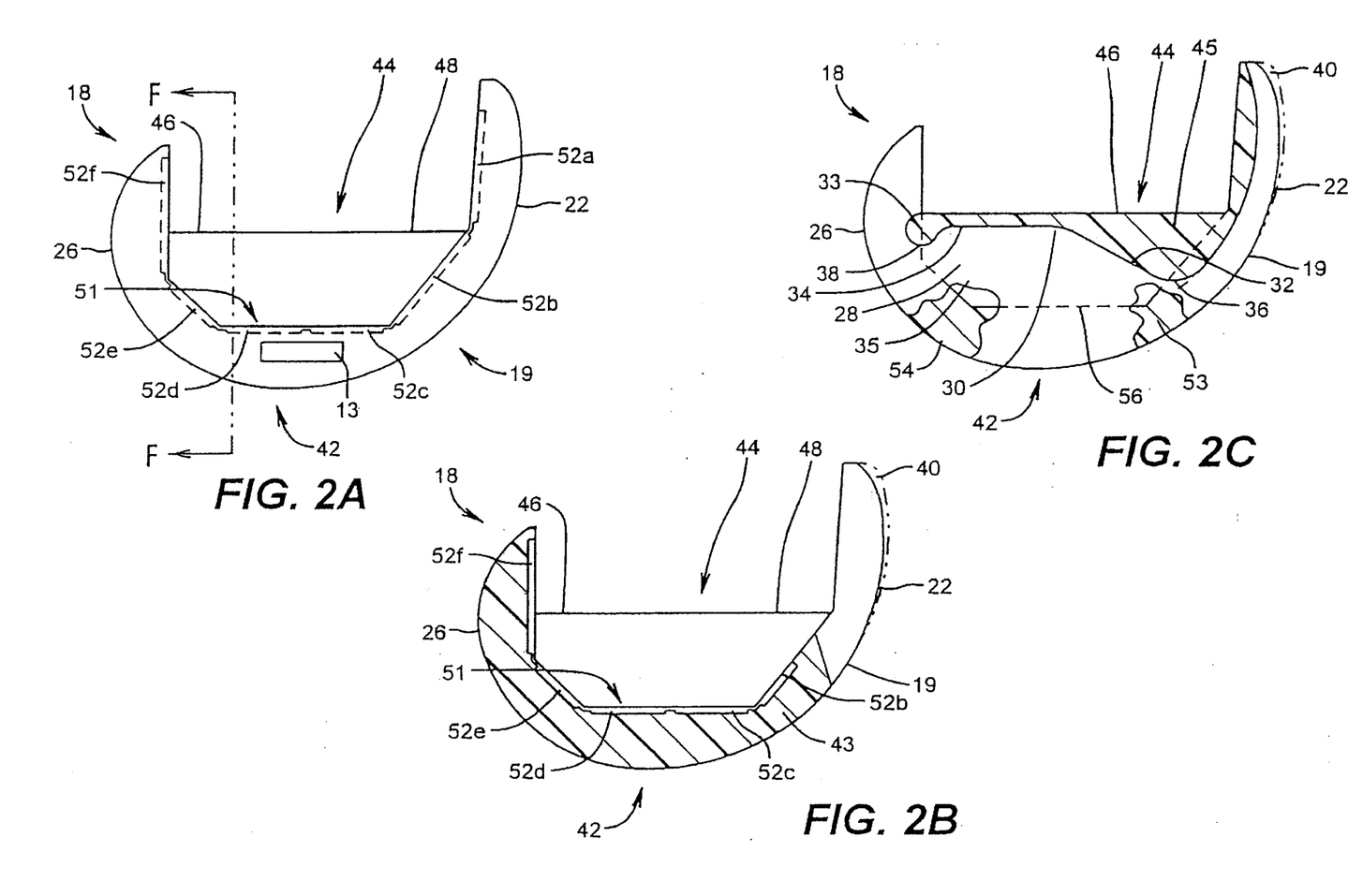

FIG. 2 is a series of views beginning with an elevational view (A), and progressing to a first sectional view (B), and ending with a bisectional view (C), of the right side 42 of distal femur component 10. FIG. 3A shows the convex curvature of the right condyle 18 along its inferior external surface 19, from its anterior portion 22 to its posterior portion 26. Recess 28 (not shown) lies under a superiorly placed box-shaped housing 44. Housing 44 has a superior wall 46 and a pair of spaced-apart lateral walls, the right of which walls 48 is shown, and the left of which walls 50 is not shown in this elevation. Superior wall 46, left wall 50, and right wall 48 are, respectively, the superior surfaces of inferior recess roof 29, and lateral recess walls left 35 and right 37 (not shown in FIG. 2). Distal femur component 10 also has a superior surface 51 variously spaced over which are right side indentations 52a–f, and similar left side indentations 54a–f (shown partially in FIG. 3A, B). Entire superior surface 51 including indentations 52a–f, 54a–f and housing 44 may be textured to enhance the attachment of the prosthesis to the resectioned femur (not shown). Posterior surface 38 may be enlarged to provide a rib surface 33 which is itself transversely concave in order to slidably interact with posterior surface 76 of tibia 60. Rib surface 33 may also act to assist in preventing subluxation.

FIG. 2B depicts section CC of FIG. 1. In particular, this sectional view shows the solid construction 43 of the underlying contour matrix. Moving in until a complete bisection of distal femur 10 along section BB of FIG. 1 can be made, FIG. 2C can be seen to expose aspects of recess 28. In this view, the pitched-roof aspects of recess 28 are clearly visible. It can be seen that the construction 45 of the body of roof 29 is solid in nature. It can also be seen through partially exposed construction at 53, 54 the solid nature of the underlying matrix. In dashed outline, juncture 56 between wall 50 of housing 44 and superior surface 51 is shown to indicate the shape of recess 28.

FIG. 3 shows sectional views of distal femur 10 shown in FIG. 1. FIG. 3A, shows section AA of FIG. 1 depicting a bisectional view of distal femur 10 from side to side and projecting toward anterior portion 22. From this view, it can be more clearly seen that anterior roof panel 32, anterior portion 36, and superior wall 46, are each transversely concavely curved. It can also be seen from this view that anterior roof panel 32 angles inferiorly from the central portions of roof 29. Condyles 16, 18 can each be seen to have external surfaces 17, 19, respectively, transversely convexly curved resulting in a smooth contour. FIG. 3B shows section JJ of FIG. 1. Steeply angled anterior roof panel 32 is most clearly seen in this view. It can also be seen that anterior portion 36 intersects anterior portions 20, 22 of condyles 16, 18, respectively, well below patellar portion 40.

FIG. 4 shows section FF of FIG. 2A transecting the distal femur laterally from its inferior to superior surfaces and projects toward its posterior. In this view, the relative positions of the right condyle 18 and left condyle 16 of distal femur 10 are reversed on the page. Indentations 52c–f, 54c–f can be seen in sequence from posterior portions 26, 24, respectively. Recess 28 opens to expose posterior roof panel 34 and posterior edge 38, both of which can be seen to be concavely transversely curved. Posterior edge 38 may further comprise a lip or rib which acts as an antisubluxation element in combination with superior edge 77 of peg 72 (as shown in FIG. 13). In certain embodiments of the invention, a theoretical antisubluxation angle 79 will be approximately 24.8°.

Figure 5A:
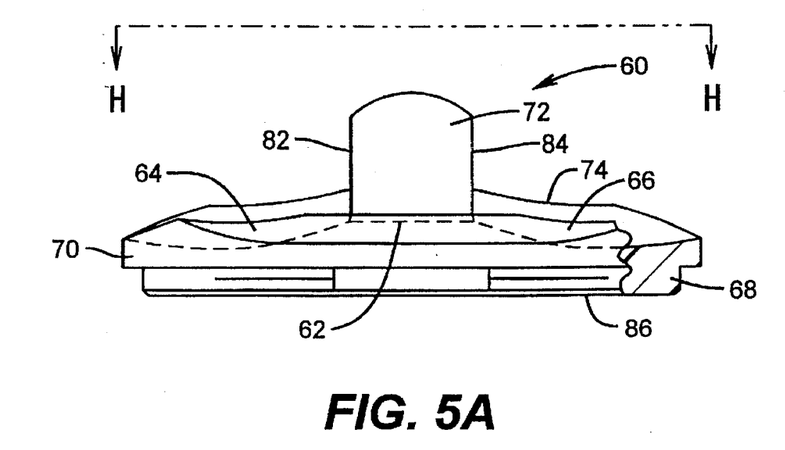
Figure 5B:
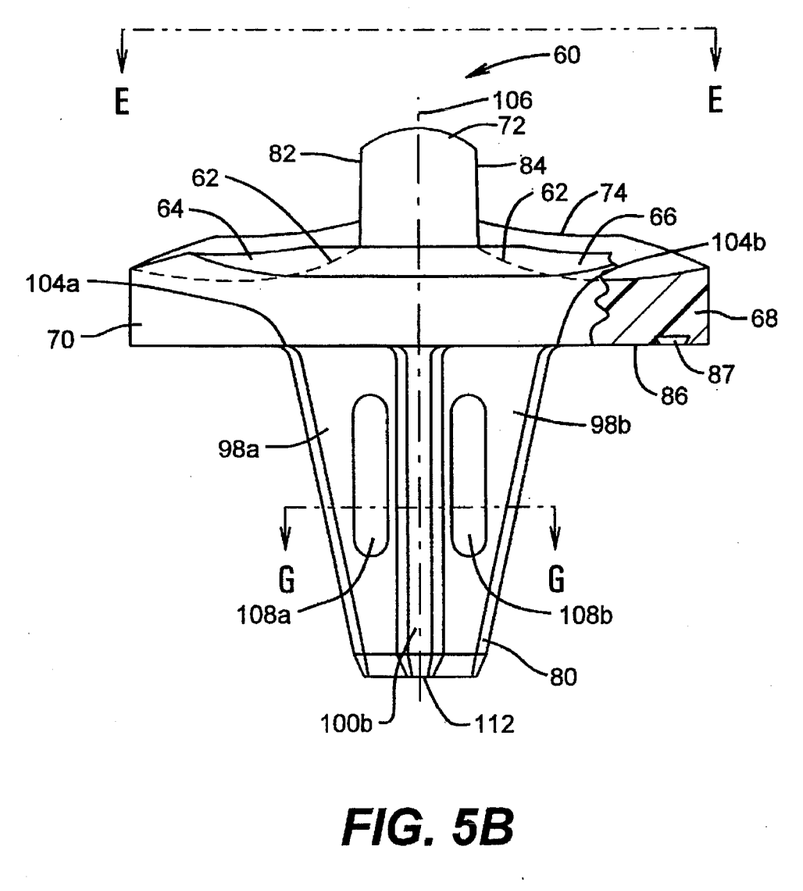

In FIG. 5, two embodiments of the proximal tibial component of the device are shown. FIG. 5A shows a posterior elevation of proximal tibial insert 60, depicting in partial dashed outline 62 the contours of left and right tibial concavities 64, 66, respectively, machined into platform 70 and laterally separated. Concavities 64, 66 provide for smooth motions resembling those motions of the natural knee including flexure and extension, when left and right condyles 16, 18 nest inside them. Underlying solid structure 68 of proximal tibia 60 is shown in partial cutaway section.

Platform 70 has wedge-shaped peg 72 located on superior surface 74. Peg 72 is laterally positioned midway between the concavities and positioned such that posterior surface 76 (the most posteriorly placed surface of the peg) is anterior to central portion 78 of tibial platform 70. Central portion 78 is found by determining the position of the mediolateral line bisecting platform 70. FIG. 5B shows a posterior side elevation of an all-polyethylene proximal tibia 70 with integral fixation post 80. Cement groove 87 may be seen in partial cutaway exposing underlying solid structure 68.

Tibial peg 72 has essentially parallel left and right lateral surfaces 82, 84, respectively. When integrated with distal femur 10, lateral surfaces 82, 84 are spaced apart from left and right lateral walls 35, 37 of pitched-roof recess 28. Lateral surfaces 82, 84 are also essentially perpendicular to base plane 86 of tibial platform 70. Tibial peg 72 also has an anterior surface 88 acutely angled in relation to base plane 86 of tibial platform 70. Posterior surface 76 is transversely curved convexly and is essentially perpendicular to base plane 86 of platform 70.

Figure 6A:
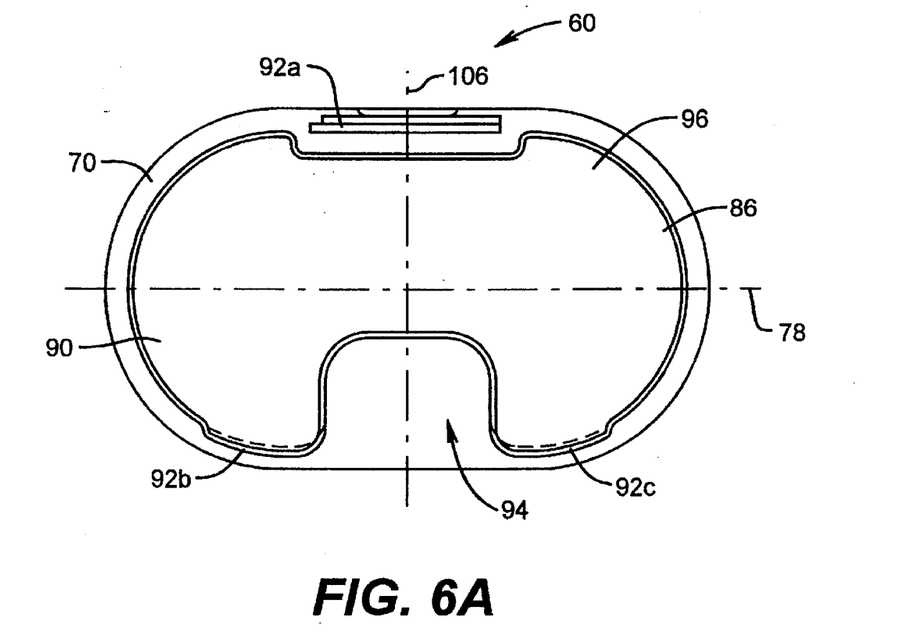
Figure 6B:
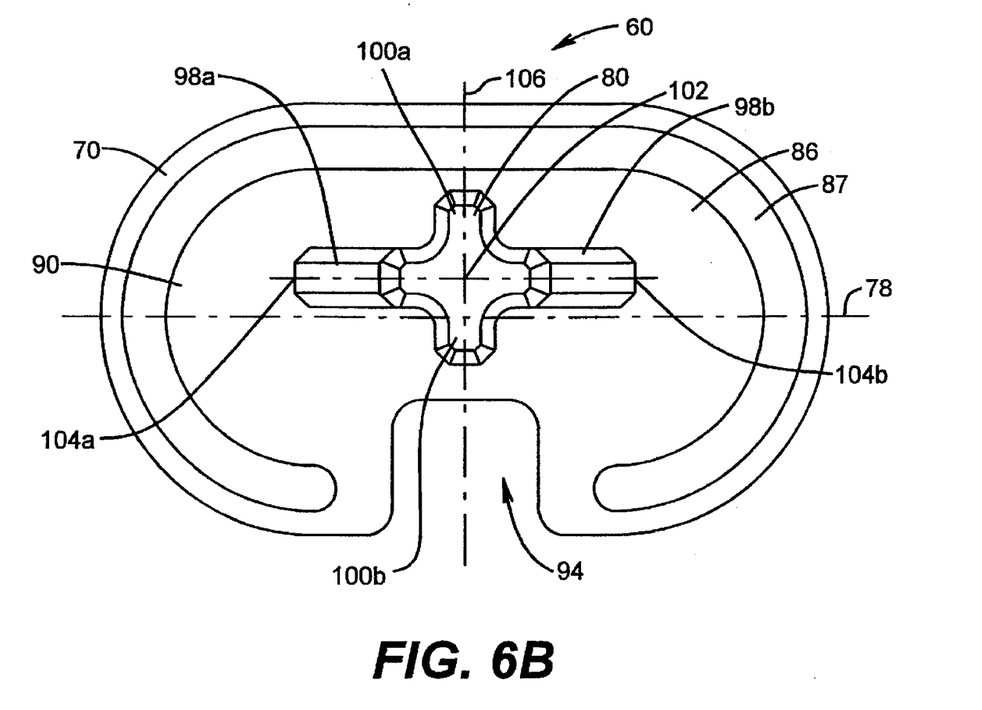

FIG. 6 shows inferior surfaces 90 in elevational views. FIG. 6A shows inferior surface 90 of proximal tibial insert 60. Inferior surface 90 has raised portion 96 designed to be fitted to a metal baseplate with a fixation post (not shown). Locking element 92a on the anterior of inferior surface 90 cooperates in conjunction with left and right locking protrusions 92b, 92c, respectively, to lock to the baseplate (not shown) to complete the assembly of a proximal tibial component 60. Indentation 94 is provided on the posterior portion of inferior surface 90 which provides adequate clearance in those instances where a universal baseplate useable with a cruciate-sparing notch is provided. FIG. 6B shows a similar inferior elevation of proximal tibial 60 with integral fixation post 80.

Integral fixation post 80 is shown as having two pairs of wings. Wider left and right lateral wings 98a, 98b, respectively, span a lateral dimension between left and right attachment points 104a, 104b equal to or greater than approximately 25% of lateral width of proximal tibia 60 as measured across mediolateral line 78. The winged portion of post 80 extends superiolaterally from inferiormost portion 112 (as shown best in FIG. 5B) to attachment points 104a, 104b on inferior surface 90. Post 80 is centered at position 102 along anteriorposterior bisecting line 106 and slightly offset anteriorly from mediolateral line 78 by approximately 3 mm. This position conforms to the I-M canal of the natural tibia (not shown) which allows easier posterior tilting of tibia 60 to approximately 7°. Narrower left and right anteroposterior wings 100a, 100b, respectively, placed perpendicular to lateral wings 98a, 98b, lie centered and parallel to line 106. Lateral wings 98a, 98b have voids 108a, 108b suitable for applying cement in their posterior surfaces (FIG. 5B), matched on their anterior surfaces with voids 110a, 110b for an all-polyethylene tibial component.

Figures 7, 8:
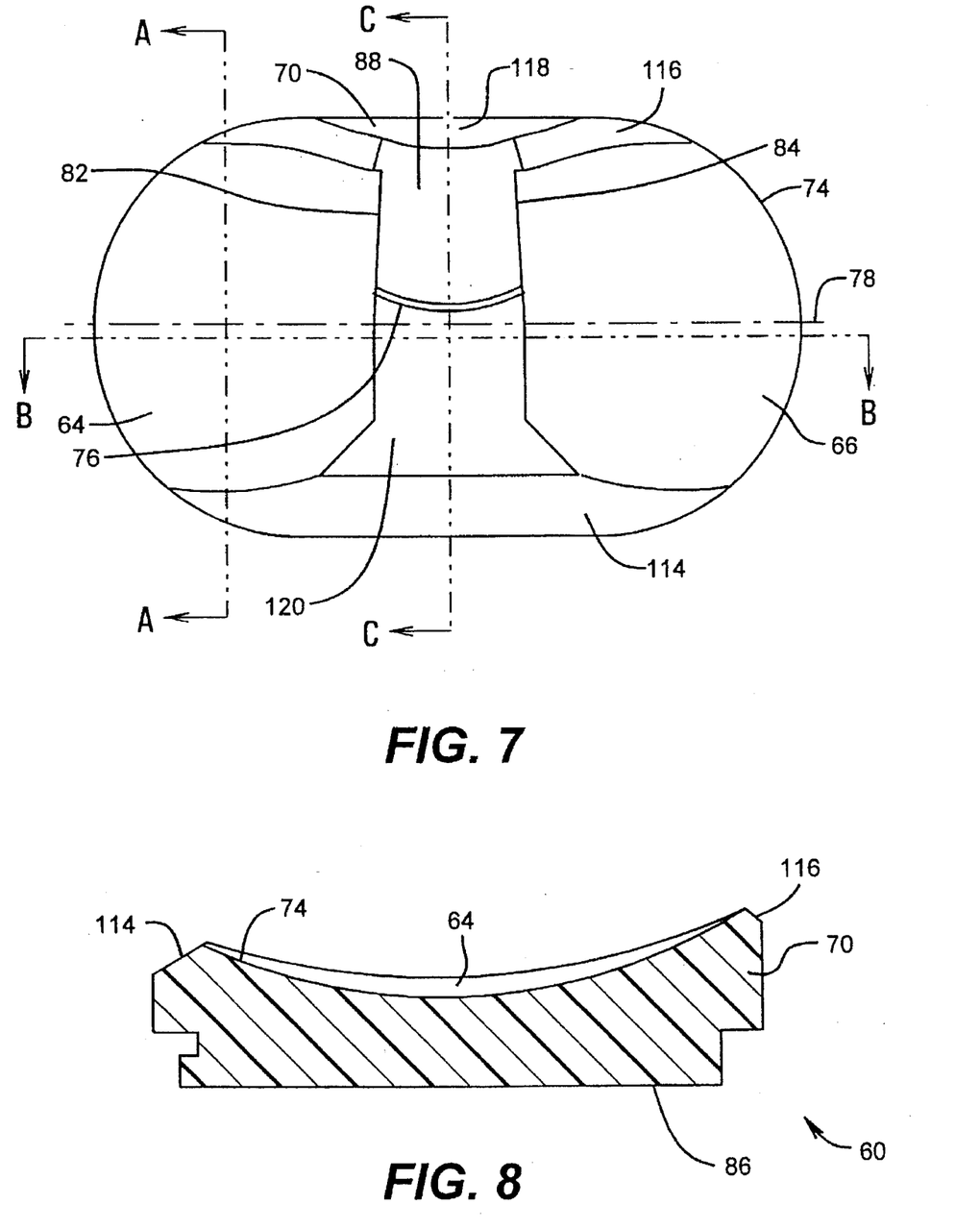
FIG. 7. View HH of FIG. 5A of a superior surface elevation of the proximal tibia (with or without integral fixation post).
FIG. 8. Section AA of FIG. 7 bisecting the proximal tibial insert, in the anterior/posterior direction across the left concavity and projecting toward the left side of the proximal tibia.

FIG. 7 shows view HH of FIG. 5A depicting superior surface 74 in an elevational view of proximal tibia 60 which view is the same whether or not proximal tibia 60 has integral fixation post 80. Posterior and anterior beveled edges 114, 116, respectively, may be included along posterior and anterior portions of proximal tibia 60. Patellar indentation 118 is located on the anterior of tibia 60 to provide additional clearance for the patella and patellar tendon (neither shown). Surface 120 is planar and parallel to base plane 86 of tibia 60 and, therefore, perpendicular to posterior surface 76 of tibial peg 72. A minor radius is shown in the figure embodiment, located at juncture 122 of planar surface 120 and posterior surface 76. Juncture 122, however, need not be a radius, but may instead be a sharp 90° angle as there is no interaction of juncture 122 and femur 10.

Figure 9A:
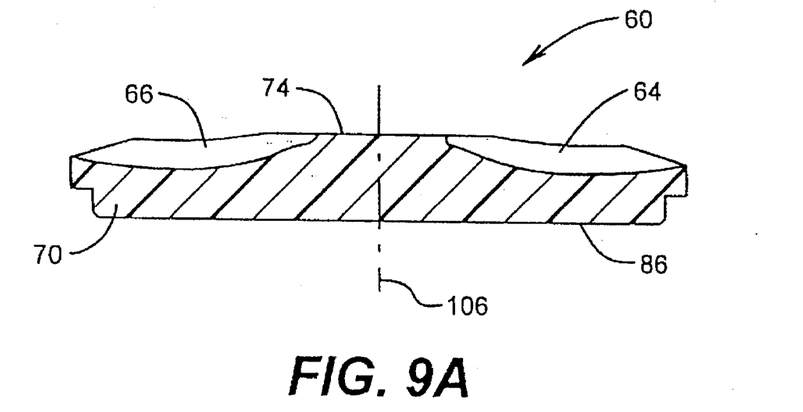
Figure 9B:
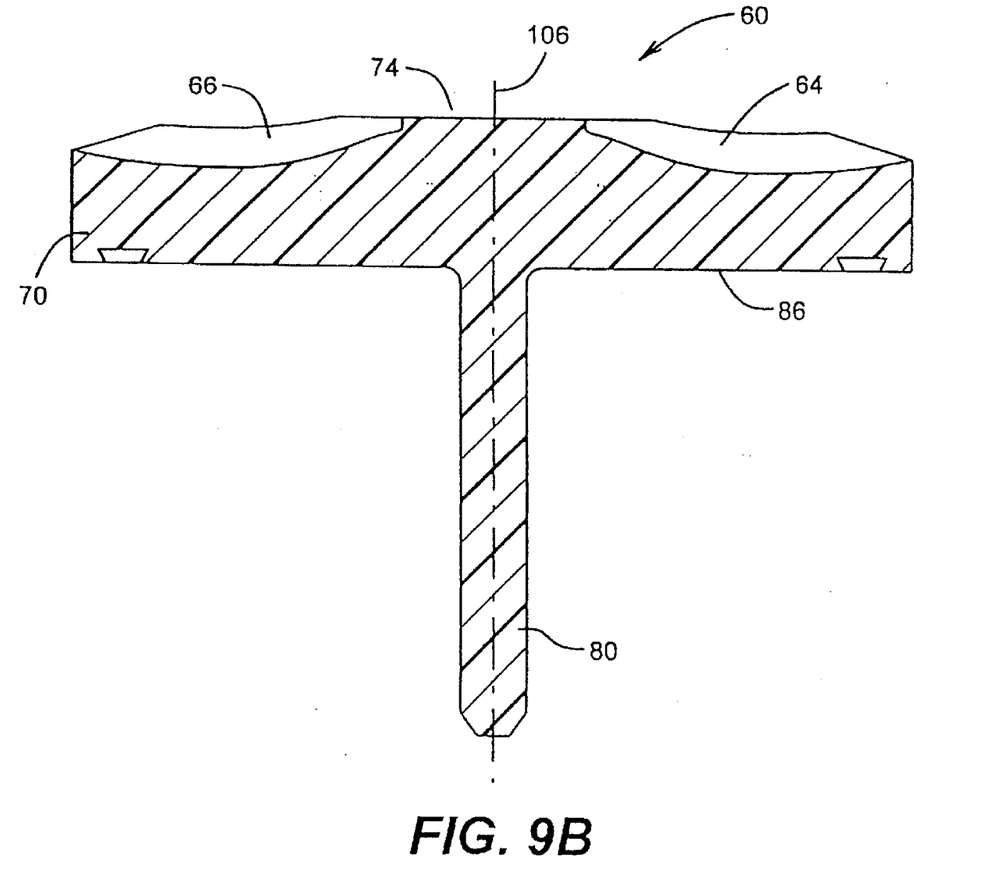

FIG. 8 shows section AA of FIG. 7 and depicts a bisection of proximal tibial insert 60 in the anterior/posterior direction across left concavity 64 and projecting toward the left side of proximal tibia 60. FIG. 9 shows sectional views of tibia 60 transversely bisected. FIG. 9A shows section BB of FIG. 7 for a tibial insert bisecting proximal tibia 60 laterally and projecting toward the posterior. FIG. 9B shows section BB of FIG. 7 for an all-polyethylene tibia with integral fixation post 80 bisecting proximal tibia 60 laterally and projecting toward the posterior.

Figure 10A:
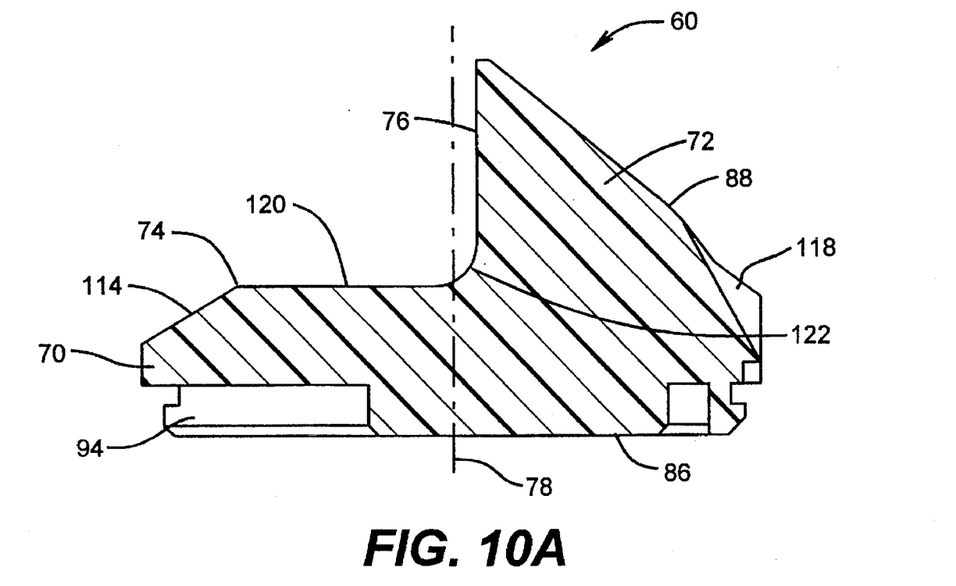
Figure 10B:
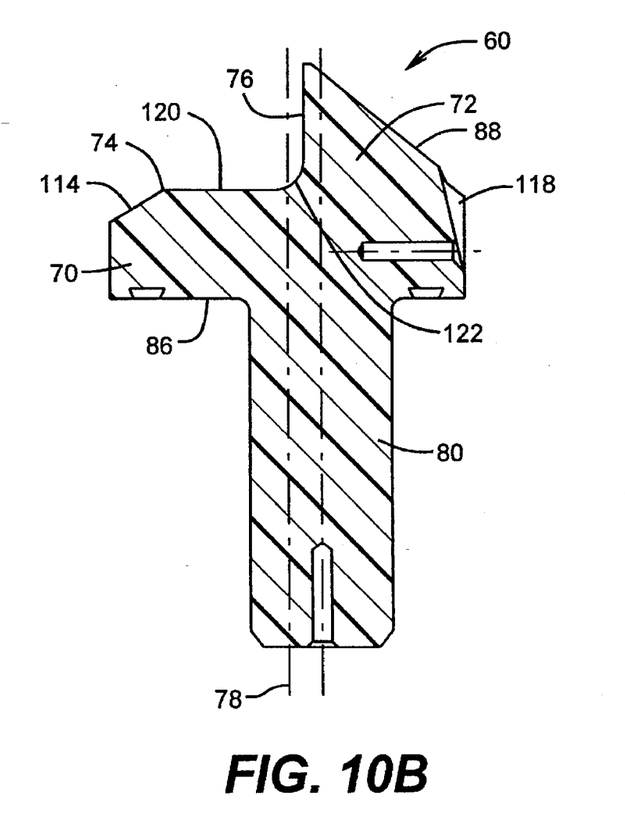

FIG. 10 shows bisectional views of tibia 60 anteriorposteriorly. FIG. 10A shows section CC of FIG. 7 bisecting proximal tibial insert 60. The bisection is accomplished in the anterior/posterior direction through a line slightly offset to the right of anterio/posterior midline 106 of proximal tibia 60 and projecting toward the left side. FIG. 10B shows section CC of FIG. 7 bisecting an all-polyethylene proximal tibia 60 manufactured with integral fixation post 80 in a similar manner.

Figure 11:
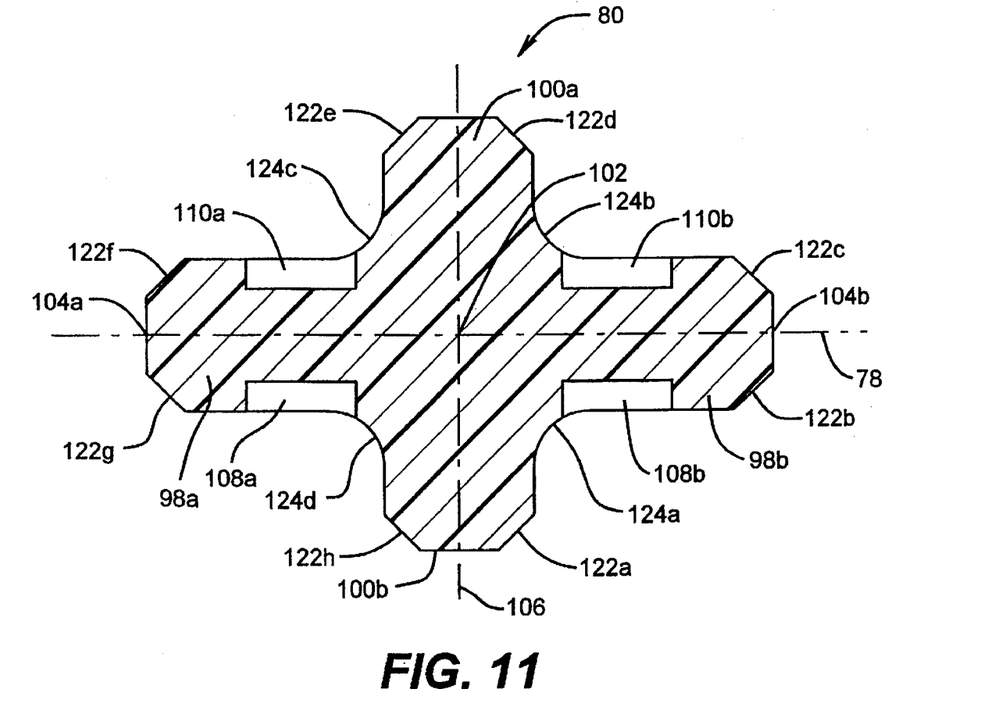
FIG. 11. Section GG of FIG. 5B laterally bisecting a middle plane of an all polyethylene tibia with fixation post and projecting inferiorly.
Figure 12A:
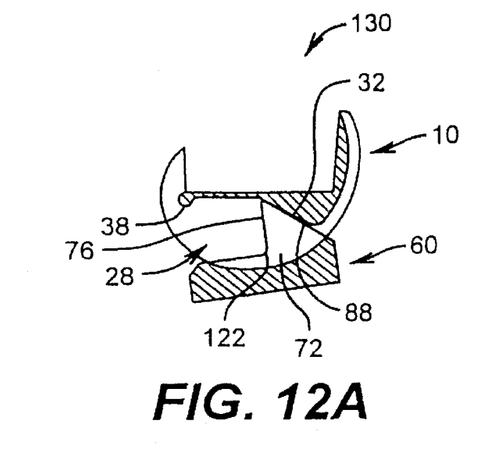

FIG. 11 shows section GG of FIG. 5B which laterally bisects a middle plane of an all-polyethylene component fixation post 80 and projects inferiorly. Both pairs of wings may be beveled on their outer corners 122a–h and may have a radius 124a–d where they meet the body of post 80. Where the body of post 80 is all-metal, voids 108a, b and 110a, b would be lacking (not shown).

FIG. 12 shows assembled knee prosthesis 130, bisected anterio-posteriorally through both components 10, 60 and depicted at a fixed 7° posterior slope. As shown, peg 72 of proximal tibia 60 is mated with recess 28 of distal femur 10. The structure of recess 28 is such that contact between recess 28 and tibial peg 72 is avoided throughout substantially all anteroposterior translation.

Figure 12B:
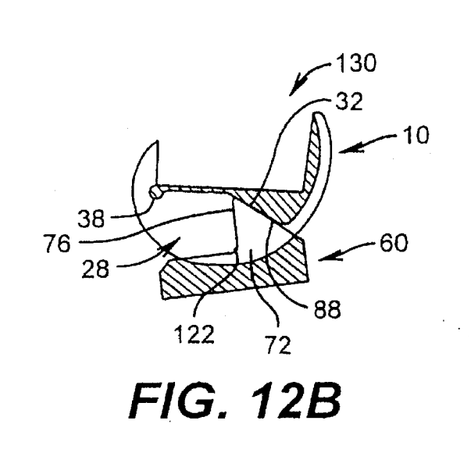
Figure 13:
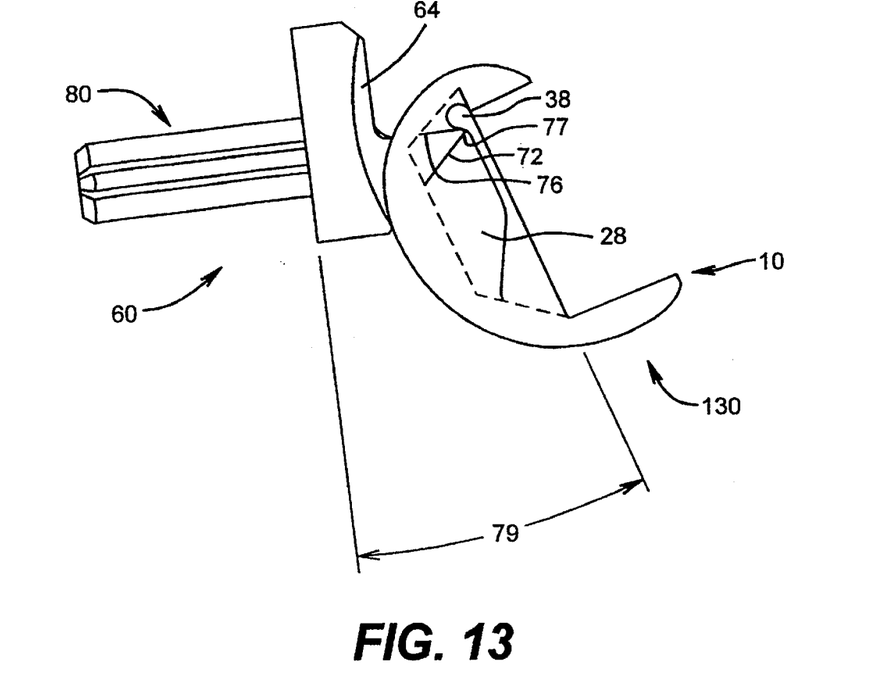
FIG. 13. Average angle of antisubluxation of assembled knee prosthesis as implanted.

FIG. 12B shows assembled knee prosthesis 130 at full extension. The relative positions and shapes of anterior surface 88 of tibial peg 72 and anterior surface 32 of recess 28 are such that, at and near full extension, anterior surfaces 32, 88 are spaced apart. This is the case even where, as shown implanted in a resectioned knee, an approximate 7° posterioral slope has been imparted to the resectioned proximal tibia. FIG. 12A shows assembled knee prosthesis 130 fully hyperextended. Peg 72 and recess 28 anterior surfaces 88, 32, respectively, remain spaced apart until at least approximately 7° to 12° of hyperextension.

Figure 12C:
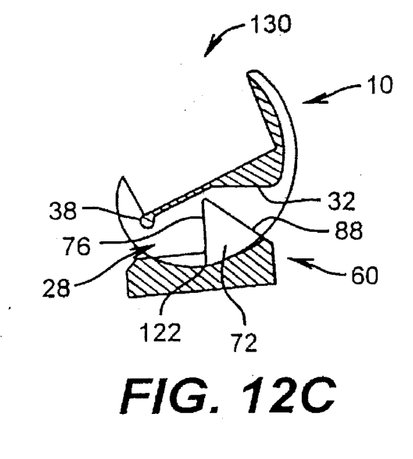
Figure 12D:
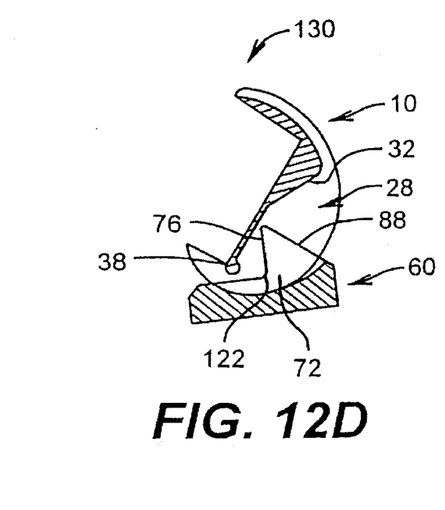

FIG. 12C shows assembled knee prosthesis 130 30° flexion. FIG. 12D shows assembled knee prosthesis 130 at 60° flexion. The first contact between the posterioral surfaces 38, 76 does not occur at or near full flexure. In certain embodiments, these posterior surfaces remain apart until at least approximately 80° to 95° of flexure.

Figure 12E:
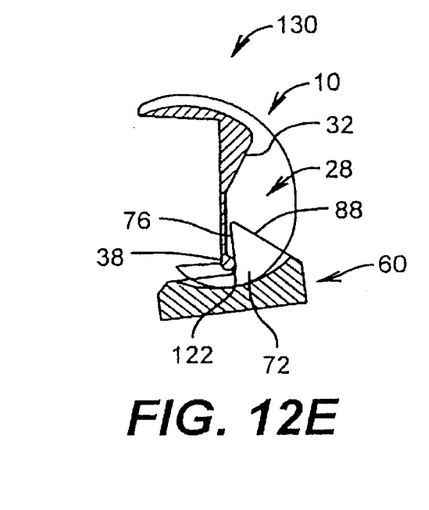

FIG. 12E shows assembled knee prosthesis 130 at angle 132 where initial contact between posterior surface 38 of distal femur 10 and posterior surface 76 of proximal tibia 60 occurs. It can be seen that first contact occurs between surface 38 and surface 76 above juncture 122.

Figure 12F:
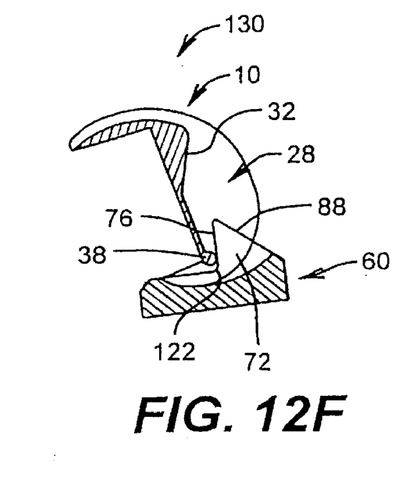

FIG. 12F shows assembled knee prosthesis 130 progressing beyond first contact. The relative positions and shapes of posterior surface 76 of tibial peg 72 and posterior surface 38 of recess 28 are constructed such that convexly curved posterior peg surface 76 matingly conforms to concavely curved surface 38. From this first contact throughout the remaining flexure motion, concavely curved posterior surface 38 stays in mated and conforming contact with convexly curved posterior surface 76 of tibial peg 60. After the initial contact between posterior surfaces 38, 76, posterior surface 38 begins an almost immediate ascent superiorly along posterior surface 76 of tibial peg 72.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

What is claimed is:

1. A knee joint prosthesis, comprising:
    a distal femur having laterally separated condyles, said condyles having external surfaces anteroposteriorly smoothly convexly curved, and laterally smoothly convexly curved substantially conforming to condylar surfaces of an anatomical femur;
    a recess joining said condyles and having spaced-apart lateral walls, an anterior roof panel, a posterior roof panel, and a peak between said roof panels; and,
    a proximal tibia having,
        a platform having laterally separated concavities, said concavities providing for smooth flexure and extension when contacting said condyles of said distal femur, and,
        a peg on a superior surface of said platform, positioned between said concavities and having a posterior surface anterior to a plane bisecting said platform into anterior and posterior portions,
        said peg configured to mate with said recess without contacting said roof panels or peak throughout substantially all anteroposterior translation of said distal femur in relation to said proximal tibia.

2. The knee joint prosthesis of claim 1, wherein said peg has essentially parallel lateral surfaces spaced apart from said lateral walls of said recess, said lateral surfaces essentially perpendicular to a base plane of said platform.

3. The knee joint prosthesis of claim 1, wherein an anterior surface of said peg is sloped posteriorly and superiorly at an acute included angle in relation to a base plane of said platform.

4. The knee joint prosthesis of claim 1, wherein relative positions and shapes of anterior surfaces of said peg and said recess are such that, at and near full extension, said anterior surfaces are spaced apart.

5. The knee joint prosthesis of claim 1, wherein said roof panels form an included angle at said peak of approximately 146° to 154°.

6. The knee joint prosthesis of claim 5, wherein said roof panels form an included angle at said peak of approximately 148° to 152°.

7. The knee joint prosthesis of claim 1, wherein said peak and said roof panels are laterally concavely curved.

8. The knee joint prosthesis of claim 1, wherein said peg includes an anterior surface, said anterior surface of said peg and said anterior roof panel of said recess remain spaced apart until at least approximately 7° to 12° of hyperextension.

9. The knee joint prosthesis of claim 1, wherein said posterior surface of said peg is essentially perpendicular to said base plane of said platform.

10. The knee joint prosthesis of claim 1, wherein said posterior surface of said peg is laterally convexly curved.

11. The knee joint prosthesis of claim 10, wherein said posterior peg surface matingly conforms to a laterally concavely curved posterior roof panel.

12. The knee joint prosthesis of claim 1, wherein said flexure is achieved without substantially shifting posteriorly points of contact between said condyles and said concavities.

13. The knee joint prosthesis of claim 12, wherein said shifting posteriorly of said points of contact is no greater than approximately 1 to 9 millimeters.

14. The knee joint prosthesis of claim 1, wherein said proximal tibia further comprises a winged fixation post on an inferior surface of said platform.

15. The knee joint prosthesis of claim 14, wherein said winged fixation post has a pair of lateral wings attached to said fixation post, and extending superiolaterally from an inferiormost portion of said fixation post to a pair of attachment points on said inferior surface, said attachment points defining a line segment having a length equal to or greater than approximately 25% of said platform's lateral width.

16. The knee joint prosthesis of claim 3, wherein relative positions and shapes of posterior surfaces of said peg and said recess are such that, at and near full flexure, said posterior surfaces are spaced apart.

17. The knee joint prosthesis of claim 16, wherein, at and near full flexure, said posterior surfaces remain spaced apart until at least approximately 80° to 95° of flexure.

18. The knee joint prosthesis of claim 17, wherein, at and near full flexure, said posterior surfaces remain spaced apart until at least approximately 84° to 93° of flexure.

19. A knee joint prosthesis, comprising:
    a distal femur having laterally separated condyles, said condyles having external surfaces anteroposteriorly smoothly convexly curved, and laterally smoothly convexly curved substantially conforming to condylar surfaces of an anatomical femur;
    a pitched-roof recess joining said condyles and having spaced-apart lateral walls, an anterior roof panel, a posterior roof panel, and a peak between said roof panels; and,
    said roof panels forming an included angle at said peak of approximately 146° to 154°,
    said peak and said roof panels being laterally concavely curved; and,
    a proximal tibia having,
        a platform having laterally separated concavities, said concavities providing for smooth flexure and extension when contacting said condyles of said distal femur, and,
        a wedge-shaped peg on a superior surface of said platform, positioned between said concavities and having a posterior surface anterior to a plane bisecting said platform into anterior and posterior portions, and having an anterior surface,
    said peg mateable with said recess without contacting said roof panels or peak throughout substantially all anteroposterior translation of said distal femur in relation to said proximal tibia,
    said peg having,
        essentially parallel lateral surfaces spaced apart from said lateral walls of said recess, said lateral surfaces essentially perpendicular to a base plane of said platform,
        an anterior surface acutely angled posteriorly and superiorly at an acute included angle in relation to said base plane of said platform, and
        a posterior surface laterally convexly curved, and essentially perpendicular to said base plane of said platform;
    relative positions and shapes of anterior surface of said peg and said anterior roof panel of said recess being such that, at and near full extension, said anterior surfaces are spaced apart and remain so until at least approximately 7° to 12° of hyperextension;

an inferior surface of said platform having a winged fixation post with a pair of lateral wings attached to said fixation post, and extending superiolaterally from an inferiormost portion of said fixation post to a pair of attachment points on said inferior surface, said attachment points defining a line segment having a length equal to approximately 25% to 50% of said platform's lateral width; and relative positions and shapes of posterior surfaces of said peg and said recess being such that, said posterior peg surface matingly conforms to said concavely curved posterior roof panel, and at and near full flexure, said posterior surfaces are spaced apart and remain so until at least approximately 80° to 95° of flexure, said flexure being achieved without substantially shifting posteriorly points of contact between said condyles and said concavities by more than approximately 1 to 9 millimeters.

* * * * *